(12) United States Patent
Albert et al.

(10) Patent No.: US 6,225,284 B1
(45) Date of Patent: *May 1, 2001

(54) SOMATOSTATIN PEPTIDES

(75) Inventors: Rainer Albert, Basel; Wilfried Bauer, Lampenberg, both of (CH); Christian Bruns, Freiburg (DE); Nagarajan Chandramouli, Morristown, NJ (US); Ian Lewis, Riehen; Gisbert Weckbecker, Biel-Benken, both of (CH)

(73) Assignee: Novartis AG, Basle (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/981,426

(22) PCT Filed: Jun. 28, 1996

(86) PCT No.: PCT/EP96/02840

§ 371 Date: Dec. 29, 1997

§ 102(e) Date: Dec. 29, 1997

(87) PCT Pub. No.: WO97/01579

PCT Pub. Date: Jan. 16, 1997

(30) Foreign Application Priority Data

Jun. 29, 1995 (GB) .................................................. 9513224
Jan. 10, 1996 (GB) .................................................. 9600429

(51) Int. Cl.[7] .......................... A61K 38/08; A61K 38/12; C07K 7/06; C07K 7/64

(52) U.S. Cl. .............................. 514/11; 514/17; 530/311; 530/329; 530/333; 530/345

(58) Field of Search ................................... 514/2, 11, 17; 530/311, 329, 333, 345

(56) References Cited

U.S. PATENT DOCUMENTS

| 3,863,008 | * | 1/1975 | Grant et al. | 424/177 |
| 4,292,972 | * | 10/1981 | Pawelchak et al. | 128/296 |
| 4,505,897 | * | 3/1985 | Coy et al. | 514/11 |
| 4,612,366 | | 9/1986 | Nutt | 530/311 |

FOREIGN PATENT DOCUMENTS

| 029 310 | 5/1981 | (EP) . |
| 389 180 | 9/1990 | (EP) . |
| 395 417 | 10/1990 | (EP) . |
| 94 00489 | 1/1994 | (WO) . |
| 95 00553 | 1/1995 | (WO) . |

OTHER PUBLICATIONS

File WPIDS on STN. No. 95–090845. WO9504752, Feb. 16, 1995 (abstract only).*

Lloyd–Williams, et al. Convergent Solid–Phase Peptide Synthesis, Tehtrahedron, vol. 49, No. 48, pp. 11065–111333, 1993.*

* cited by examiner

*Primary Examiner*—Christopher S. F. Low
*Assistant Examiner*—Anish Gupta
(74) *Attorney, Agent, or Firm*—Joseph J. Borovian

(57) ABSTRACT

Somatostain analogues comprising the amino acid sequence of the formula (I): -(D/L)Trp-Lys-$X_1$-$X_2$, wherein $X_1$ is a substituted Thr, Ser, Tyr, Glu or Cys residue and $X_2$ is an α-amino acid having an aromatic residue on the $C_\alpha$ side chain, or an amino acid unit selected from Dab, Dpr, Dpm, His (Bzl)HyPro, thienyl-Ala, cyclohexyl-Ala and t.-butyl-Ala, the residue Lys of said sequence corresponding to the residue $Lys^9$ of the native somatostatin-14, in free form, in salt form or complexed with a detectable element have interesting pharmacological properties.

7 Claims, No Drawings

SOMATOSTATIN PEPTIDES

The present invention relates to somatostatin peptides, a process for their production and pharmaceutical preparations containing them.

Somatostatin is a tetradecapeptide having the structure:

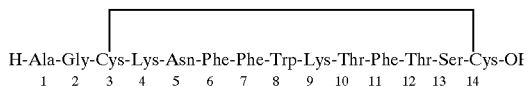

Since the isolation and characterization of somatostatin, an extensive search for more potent and more stable analogues has continued.

More particularly the present invention provides a somatostatin analogue comprising the amino acid sequence of formula (I)

           (I)

wherein $X_1$ is a radical of formula (a) or (b)

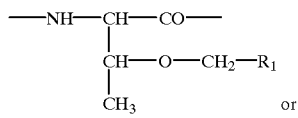

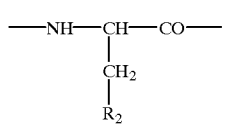

wherein $R_1$ is optionally substituted phenyl,
$R_2$ is $-Z_1-CH_2-R_1$, $-CH_2-CO-O-CH_2-R_1$,

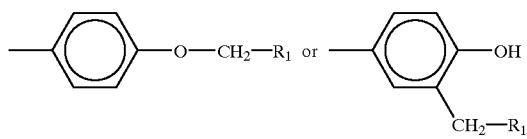

wherein $Z_1$ is O or S, and $X_2$ is an α-amino acid having an aromatic residue on the $C_\alpha$ side chain, or an amino acid unit selected from Dab, Dpr, Dpm, His,(Bzl)HyPro, thienyl-Ala, cyclohexyl-Ala and t.-butyl-Ala, the residue Lys of said sequence corresponding to the residue $Lys^9$ of the native somatostatin-14.

These compounds are referred to hereinafter as COMPOUNDS OF THE INVENTION.

By somatostatin analogue as used herein is meant a straight-chain or cyclic peptide derived from that of the naturally occurring somatostatin-14, comprising the sequence of formula I and wherein additionally one or more amino acid units have been omitted and/or replaced by one or more other amino acid radical(s) and/or wherein one or more functional groups have been replaced by one or more other functional groups and/or one or more groups have been replaced by one or several other isosteric groups. In general the term covers all modified derivatives of the native somatostatin-14 comprising the above sequence of formula I which have binding affinity in the nM range to at least one somatostatin receptor subtype as defined hereinafter.

According to a preferred embodiment of the invention, there is provided a somatostatin analogue in which the residues at positions 8 through 11 of the somatostatin-14 are represented by the sequence of formula I as defined above.

More preferably there is provided a somatostatin analogue as disclosed above comprising a hexapeptide unit, the residues at positions 3 through 6 of said hexapeptide unit comprising the sequence of formula I. Particularly preferred is a somatostatin hexapeptide wherein the residues at positions 1 and 2 of the hexapeptide unit may be any of those as known in the art, e.g. as disclosed by A. S. Dutta in Small Peptides, Vol.19, 292–354, Elsevier, 1993, or as substituents for, $Phe^6$ and/or $Phe^7$ of somatostatin-14.

More particularly there is provided a somatostatin analogue in which the hexapeptide unit is cyclic, e.g. having a direct peptide linkage between the a-carbonyl group of the residue at position 6 and the α-amino group of the residue at position 1.

While Lys, $X_1$ and $X_2$ in the sequence of formula I have the L-configuration, Trp may have the D- or L-configuration. Preferably Trp has the D-configuration.

$X_1$ is preferably a residue of formula (a) or (b), $R_2$ being preferably

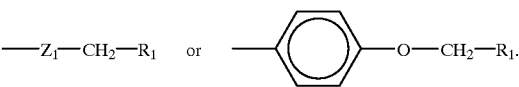

When $X_2$ comprises an aromatic residue on the $C_\alpha$ side chain, it may suitably be a natural or unnatural α-amino acid, e.g. Phe, Tyr, Trp, Nal, Pal, benzothienyl-Ala, Tic and thyronin, preferably Phe or Nal, more preferably Phe. $X_2$ is preferably an α-amino acid bearing an aromatic residue on the $C_\alpha$ side chain.

When $R_1$ is substituted phenyl, it may suitably be substituted by halogen, methyl, ethyl, methoxy or ethoxy e.g. in ortho and/or para. More preferably $R_1$ is unsubstituted phenyl.

$Z_1$ is preferably O.

Representative COMPOUNDS OF THE INVENTION are e.g a compound of formula (II)

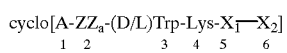       (II)

wherein $X_1$ and $X_2$ are as defined above,

A is a divalent residue selected from Pro,

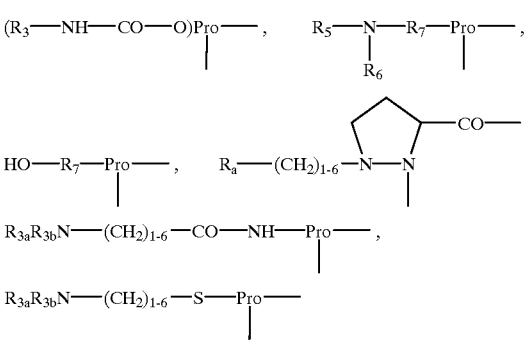

-continued

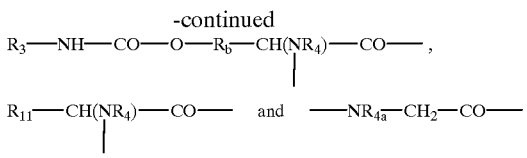

wherein $R_3$ is $NR_8R_9$—$C_{2-6}$alkylene, guanidino-$C_{2-6}$alkylene or $C_{2-6}$alkylene-COOH, $R_{3a}$ is H, $C_{1-4}$alkyl or has independently one of the significances given for $R_3$. $R_{3b}$ is H or $C_{1-4}$alkyl, $R_a$ is OH or $NR_5R_6$, $R_b$ is —$(CH_2)_{1-3}$— or —$CH(CH_3)$—, $R_4$ is H or $CH_3$, $R_{4a}$ is optionally ring-substituted benzyl, each of $R_5$ and $R_6$ independently is H, $C_{1-4}$alkyl, ω-amino-$C_{1-4}$alkylene, ω-hydroxy-$C_{1-4}$alkylene or acyl, $R_7$ is a direct bond or $C_{1-6}$alkylene, each of $R_8$ and $R_9$ independently is H, $C_{1-4}$alkyl, ω-hydroxy-$C_{2-4}$alkylene, acyl or $CH_2OH$—$(CHOH)_c$—$CH_2$— wherein c is 0, 1, 2, 3 or 4, or $R_8$ and $R_9$ form together with the nitrogen atom to which they are attached a heterocyclic group which may comprise a further heteroatom, and $R_{11}$ is optionally ring-substituted benzyl, —$(CH_2)_{1-3}$—OH, $CH_3$—CH(OH)— or —$(CH_2)_{1-5}$—$NR_5R_6$, and $ZZ_a$ is a natural or unnatural α-amino acid unit.

$ZZ_a$ may have the D- or L-configuration. When $ZZ_a$ is a natural or unnatural α-amino acid unit, it may suitably be e.g. Thr, Ser, Ala, Val, Ile, Leu, Nle, His, Arg, Lys, Nal, Pal, Tyr, Trp, optionally ring-substituted Phe or $N^α$-benzyl-Gly. When $ZZ_a$ is Phe, the benzene ring thereof may be substituted by e.g. $NH_2$, $NO_2$, $CH_3$, $OCH_3$ or halogen, preferably in para position. When $ZZ_a$ is Phe, the benzene ring thereof is preferably unsubstituted.

When A comprises a Pro amino acid residue, any substituent present on the proline ring, e.g. $R_3$—NH—CO—O— etc., is preferably in position 4. Such substituted proline residue may exist in the cis form, e.g.

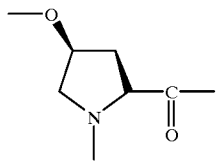

as well as in the trans form. The present invention covers each geometric isomer individually as well as mixtures thereof.

When A is

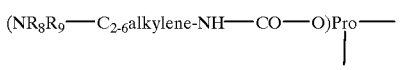

where $NR_8R_9$ forms a heterocyclic group, such group may be aromatic or saturated and may comprise one nitrogen or one nitrogen and a second heteroatom selected from nitrogen and oxygen. Preferably the heterocyclic group is e.g. pyridyl or morpholino. $C_{2-6}$Alkylene in this residue is preferably —$CH_2$—$CH_2$—.

Any acyl as $R_5$, $R_6$, $R_8$ and $R_9$ in A may be e.g. $R_{12}CO$— wherein $R_{12}$ is H, $C_{1-4}$alkyl, $C_{2-4}$alkenyl, $C_{3-6}$cycloalkyl or benzyl, preferably methyl or ethyl. When $R_{4a}$ or $R_{11}$ in A is ring-substituted benzyl, the benzene ring may be substituted as indicated above for $ZZ_a$.

A preferred group of COMPOUNDS OF THE INVENTION is e.g compounds of formula II wherein A is free of a lateral —NH—CO—O— moiety. A further group of preferred COMPOUNDS OF THE INVENTION is e.g. compounds of formula II wherein A comprises a basic lateral radical, e.g. a $R_3$—NH—CO—O— or

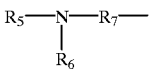

moiety.

A still further group of preferred COMPOUNDS OF THE INVENTION is the group of compounds wherein the N-terminal amino acid comprises a substituted Pro, particularly 4-substituted Pro, e.g. compounds of formula II wherein A is 4-substituted Pro.

Preferably A is 4-($R_3$—NH—CO—O)Pro.

Further representative COMPOUNDS OF THE INVENTION are such compounds comprising an amino group bearing a chelating group, particularly a compound of formula II wherein A comprises a side chain amino group which bears a chelating group, in free form, in salt form or complexed with a detectable element. These compounds are referred hereinto as chelated COMPOUNDS OF THE INVENTION.

Suitable chelating groups are physiologically acceptable chelating groups capable of complexing a detectable element. Preferably the chelating group has a substantially hydrophilic character. Examples of chelating groups include e.g. those derived from polyaminopolycarboxylic acids or anhydrides, e.g. those derived from non cyclic ligands e.g. ethylene diaminetetraacetic acid (EDTA), diethylene triamine pentaacetic acid (DTPA), ethylene glycol-0,0'-bis(2-aminoethyl)-N,N,N',N'-tetraacetic acid (EGTA), N,N'-bis(hydroxybenzyl)ethylenediamine-N,N'-diacetic acid (HBED) and triethylenetetramine hexaacetic acid (TTHA), those derived from substituted EDTA or DTPA, e.g. p-isothiocyanato-benzyl-EDTA or -DTPA, those derived from macrocyclic ligands, e.g. 1,4,7,10-tetra-azacyclododecane-N,N',N'',N'''-tetraacetic acid (DOTA) and 1,4,8,11-tetraazacyclotetradecane-N,N',N'',N'''-tetraacetic acid (TETA), or 1,4,7,10-tetraazacyclotridecane-N,N',N'',N'''-tetraacetic acid (TITRA).

The chelating group may be attached either directly or through a spacer to the amino group of the COMPOUND OF THE INVENTION. suitable spacers include those known in the art, e.g. as disclosed in GB-A-2,225,579, for example the divalent residue of an amino-carboxylic acid, for example β-Ala or a divalent residue derived from 6-amino-caproic acid.

Preferred chelating groups are those derived from DTPA, DOTA, TETA or substituted EDTA or DTPA. Chelating groups derived from DTPA or DOTA are most preferred.

By detectable element is meant any element, preferably a metal ion which exhibits a property detectable in therapeutic or afi diagnostic techniques, e.g. a metal ion which emits a detectable radiation or a metal ion which is capable of influencing NMR relaxation properties.

Suitable detectable metal ions include for example heavy elements or rare earth ions, e.g. as used in CAT scanning (Computer axial tomography), paramagnetic ions, e.g. $Gd^{3+}$, $Fe^{3+}$, $Mn^{2+}$ and $Cr^{2+}$, fluorescent metal ions, e.g. $Eu^{3+}$, and radionuclides, e.g. a radiolanthanide, particularly γ-emitting radionuclides, β-emitting radionuclides, α-emitting radionuclides, Auger-e⁻-emitting radionuclides, positron-emitting radionuclides e.g. $^{68}$Ga.

Suitable γ-emitting radionuclides include those which are useful in diagnostic techniques. The γ-emitting radionuclides advantageously have a half-life of from 1 hour to 40 days, preferably from 5 hours to 4 days, more preferably from 12 hours to 3 days. Examples are radionuclides derived from Gallium, Indium, Technetium, Ytterbium, Rhenium, Terbium, Thallium and Samarium e.g. $^{67}$Ga, $^{111}$In, $^{99m}$Tc, $^{161}$Tb, $^{169}$Yb and $^{186}$Re.

Suitable β-emitting radionuclides include those which are useful in therapeutic applications, for example $^{90}$Y, $^{67}$Cu, $^{186}$Re, $^{188}$Re, $^{169}$Er, $^{121}$Sn, $^{127}$Te, $^{143}$Pr, $^{198}$Au, $^{109}$Pd, $^{165}$Dy, $^{32}$P, $^{142}$Pr and $^{156}$Sm Suitable α-emitting radionuclides are those which are used in therapeutic treatments, e.g. $^{211}$At, $^{212}$Bi or $^{201}$Tl.

The COMPOUNDS OF THE INVENTION may exist e.g. in free or salt form. Salts include acid addition salts with e.g. organic acids, polymeric acids or inorganic acids, for example hydrochlorides and acetates and salt forms obtainable with the carboxylic acid groups when present e.g in the chelating group, e.g. alkali metal salts such as sodium or potassium, or substituted or unsubstituted ammonium salts.

The present invention also includes a process for the production of the COMPOUNDS OF THE INVENTION. They may be produced by analogy to known methods.

The COMPOUNDS OF THE INVENTION may be produced for example as follows:
  a) removing at least one protecting group which is present in a somatostatin peptide comprising a residue of formula I, the somatostatin peptide being in protected form, or
  b) linking together by an amide bond two peptide units, each of them containing at least one amino acid in protected or unprotected form, wherein the amide bond is in such a way that the desired amino acid sequence is obtained and, where required, effecting process step a), or
  c) removing a functional group of an unprotected or a protected somatostatin peptide or converting it into another functional group so that another unprotected or protected peptide is obtained and in the latter case stage a) of the process is effected, or
  d) to produce a chelated COMPOUND OF THE INVENTION linking together a chelating agent and a non-chelated COMPOUND OF THE INVENTION in protected or unprotected form and comprising a free amino group in such a way that the chelating group is fixed on the desired amino group of the COMPOUND, and stage a) is then optionally effected
and recovering the COMPOUNDS OF THE INVENTION thus obtained in free form, in salt form or optionally complexed with a detectable element.

Process step b) leads to the preparation of a linear peptide but includes also the cyclization by an amide bond of a linear peptide to give a cyclic peptide having the desired amino acid sequence. If desired, the lateral chain present in A may be introduced on the amino acid prior to the peptide coupling step b) or on the final linear or cyclic peptide according to step c). Thus, in the latter case, a compound of formula II wherein A is hydroxy-Pro may be converted to provide a compound of formula II wherein A is $R_3$—NH—CO—O-Pro.

Cyclization may also conveniently be performed via the hydrazide. When the linear peptide is prepared on the resin, it is generally not critical which amino acid is selected to be at the C-terminal position provided only that the sequence of amino acids in the linear peptide corresponds to that in the desired somatostatin analog. Once a linear peptide has been cyclized one can no longer determine which amino acid was at the C-terminus of the linear peptide. While generally the selection of the first amino acid to start the chain is not critical, since the linear peptide will be cyclized, there may be other factors which may prefer one starting amino acid over another. Preferably the linear peptide is cyclized in such a way to produce a bond from Trp in position 3 to $ZZ_a$ in position 2 or from $X_2$ in position 6 to $X_1$ in position 5.

The complexation of a COMPOUND OF THE INVENTION comprising an amino group substituted by a chelating group may be performed by reacting the chelated COMPOUND with a corresponding detectable element yielding compound, e.g. a metal salt, preferably a water-soluble salt. The reaction may be carried out by analogy with known methods, e.g. as disclosed in Perrin, Organic Ligand, Chemical Data Series 22. NY Pergamon Press (1982); in Krejcarit and Tucker, Biophys. Biochem. Res. Com. 77: 581 (1977) and in Wagner and Welch, J. Nucl. Med. 20: 428 (1979).

Insofar as the production of the starting materials is not particularly described, the compounds are known or may be prepared analogously to methods known and practiced in the art.

The following examples are illustrative of the invention. All temperatures are in ° C.

The following abbreviations are used:
Bzl=benzyl (Bzl)=—CH$_2$-phenyl attached to an oxygen or sulfur according to (a) or (b)
DMF=dimethylformamide
BOC=tert. butyloxycarbonyl
Fmoc=9-fluorenylmethoxycarbonyl
TFA=trifluoroacetic acid
DIPCI=diisopropylcarbodiimide
DCCI=dicyclohexyl carbodiimide
HOBt=hydroxybenzotriazole
Dab=2,4-diaminobutyric acid
Dpr=2,3-diaminopropanoic acid
Dpm=2,6-diaminoheptanedioic acid
Dde=4,4-dimethyl-2,6-dioxocyclohex-1-ylidene ethyl
RT=room temperature
HyPro=4-hydroxy-Pro (trans except where otherwise stated)
Tic=Tetrahydroisoiuinoline-carboxylic acid

EXAMPLE 1

Cyclo [HyPro-Phe-DTrp-Lys-Tyr(Bzl)-Phe]

Fmoc-Phe-SASRIN® Resin (1.00 g, 0.65 7mol) is carried through the procedures of Fmoc solid phase synthesis until the desired Fmoc-(D)Trp-Lys(Boc)-Tyr(Bzl)-Phe-Pro(y-t-OH)-Phe SASRIN® peptide resin is assembled. The Fmoc is deprotected using piperidine. Cleavage of the peptide resin is carried out using hydrazinolysis. To 1.00 g of the peptibde resin, 8.3 ml of DMF and 1.24 ml of hydrazine hydrate (ca. 15% hydrazine hydrate in DMF) is added. The mixture is stirred for 15 hours at RT. After the reaction the resin is filtered and washed well with DMF. The filtrate is collected and evaporated in high vacuo to give an oily hydrazide product residue. The residue is dissolved in water and lyophilized to give 480 mg of linear H-(D)Trp-Lys(Boc)-Tyr(Bzl)-Phe-HyPro-Phe-NH-NH$_2$ hydrazide product. This hydrazide is dissolved in 16 ml DMF, cooled to −20° and is treated with 4N HCl in ether (2.4 ml, 11.6 mmol) and subsequently tert.-butylnitrite (41.3 μl, 0.348 mmol). The reaction is stirred for 20 minutes. Diisopropylethylamine (11.6 mmol, 2 ml) is added and the reaction is stirred for 72 h at room temperature. After the reaction is complete, DMF is removed under high vacuum. Water is added to the oily residue, leading to a precipitation. Extraction is carried out between ethyl acetate and water. The organic phases are dried over sodium sulphate and the product is isolated. Deprotection is carried out using TFA/water 95:5 and the product is isolated using reversed phase HPLC. Ion exchange of the product containing fractions is performed and lyophilization gives the title product as a white powder, MH$^+$(FAB) 975, F=1.24 [α]$^D_{22}$=+39.0° (95% AcOH; c=0.1)

EXAMPLE 2

Cyclo[{4-(NH$_2$—C$_2$H$_4$—NH—CO—O—)Pro}-Phe-DTrp-Lys-Tyr(Bzl)-Phe]

Fmoc-HyPro-OMe is added dropwise into a solution of trisphosgene (0.6 eq.) in THF. After 1 h dimethylaminopyridine (1.0 eq.) and N-BOC-diaminoethane (6.0 eq.) are added and the reaction is stirred at RT. After TLC studies, solvent is removed in vacuo and the Fmoc-4-(N-BOC-aminoethylaminocarbonyloxy)Pro-OMe is extracted from a two phase system of ethylacetate/0.1 M HCl to give crude product (MH$^+$=554). The crude methyl ester isolated above is then cleaved to the free acid by treatment with 1N NaOH in dioxane/water and the product Fmoc-4-(aminoethylaminocarbonyloxy)-Pro-OH is purified on silica gel, (MNa)$^+$=562).

Fmoc-Phe-SASRIN® Resin (1.0 g, 0.65 mmol) is carried through the procedures of Fmoc solid phase synthesis until the desired Fmoc-(D)Trp(BOC)-Lys(Boc)-Tyr(Bzl)-Phe-Pro(γ-t-N-BOC-diaminoethanecarbamoyl)-Phe-SASRIN peptide resin is assembled. The Fmoc is deprotected using piperidine. Cleavage of the peptide resin is carried out by treating the peptide resin in a glass column with 2% TFA in CH$_2$Cl$_2$. Neutralization is carried out with 1M NaHCO$_3$ solution. The solvent is evaporated in vacuo and the protected linear peptide is lyophilized (MH$^+$=1379.8). The protected linear peptide is cyclized by treatment with DCCI (6.0 eq.) and HOBt (6.0 eq.) over a period of 5 days.

Deprotection is then achieved with 95:5 TFA:H$_2$O, and the cyclic peptide is purified by preparative HPLC and ion exchanged to the acetate salt form with AG4-X4 ion exchange resin to give the title compound (FAB-MH$^+$= 1061.7).

EXAMPLE 3

Cyclo[{4-(morpholino-ethyl-aminocarbonyloxy)-Pro}-Phe-DTrp-Lys-Tyr(Bzl)-Phe]

The synthesis of the hydroxyproline-extension is as follows: Fmoc-HyPro-OMe is added dropwise into a solution of trisphosgene (0.6 eq.) in THF. After 1 h dimethylaminopyridine (1.0 eq.) and N-ethylaminomorpholine (6.0 eq.) are added and the reaction is stirred at RT. After TLC studies, solvent is removed in vacuo and the Fmoc-4-(morpholinoethylaminocarbonyloxy)Pro-OMe is purified on silica gel, (MH$^+$ 524). The methyl ester is then cleaved by treatment with 1N NaOH in dioxane/water and the product Fmoc-4-(morpholinoethylaminocarbonyloxy)Pro-OH is purified on silica gel, (MH$^+$ 510).

Fmoc-Phe-SASRIN is taken through the procedures of Fmoc solid phase synthesis in a manner analogous to the previous example until the desired Fmoc-(D)Trp(Boc)-Lys(Boc)-Tyr(Bzl)-Phe-(Morpholinoethylaminocarbamate)HyPro-Phe-SASRIN resin is assembled. The Fmoc is deprotected using piperidine. Cleavage of the peptide resin is carried out by treating the peptide resin in a glass column with 2% TFA in CH$_2$Cl$_2$. Neutralization is carried out with 1M NaHCO$_3$ solution. The solvent is reduced in vacuo and the protected linear peptide is lyophilized. The protected linear peptide is cyclized by treatment with DCCI (6.0 eq.) and HOBt (6.0 eq.) over a period of 5 days. Deprotection is then achieved with 95:5 TFA:H$_2$O and the cyclic peptide is purified by preparative HPLC and ion exchanged to the acetate salt form with AG4-X4 ion exchange resin to give the title compound.

MH$^{30}$ (FAB): 1131 [α]$^D_{22}$=−55.0° (95% AcOH; c=0.1)

By repeating the procedures as disclosed above but using the corresponding starting materials, compounds of formula cyclo[X-Y-DTrp-Lys-Z-Phe]

wherein X, Y and Z are as defined in Table 1 below, may be obtained.

TABLE 1

| Ex. | X | Y | Z | Physico-chemical Data MH$^+$ | |
|-----|---|---|---|---|---|
| 4 | 4-HyPro | N$^α$-Bzl-Gly | Tyr(Bzl) | E.S. | 975.7 |
| 5 | Pro | Phe | Tyr(Bzl) | FAB | 959 |
| 6 | 4-(NH$_2$—C$_2$H$_4$—NH—CO—O—)Pro | His | Tyr(Bzl) | E.S. | 1051.5 |
| 7 | id. | Tyr | Tyr(Bzl) | FAB | 1077 |
| 8 | id. | Arg | Tyr(Bzl) | E.S. | 1070.4 |
| 9 | 4-(NH$_2$—C$_3$H$_6$—NH—CO—O—)Pro | His | Tyr(Bzl) | E.S. | 1065.4 |
| 10 | id. | Phe | Tyr(Bzl) | FAB | 1075 |
| 11 | id. | Tyr | Tyr(Bzl) | E.S. | 1091.7 |
| 12 | 4-(NH$_2$—C$_2$H$_4$—NH—CO—O—)Pro | Phe | Ser(pClBzl) | E.S. | 1019.6 |
| 13 | id. | Ala | Thr(Bzl) | E.S. | 924.2 |
| 14 | id. | Phe | Tyr(Bzl) | FAB | 1047 |
| 15 | id. | Trp | Tyr(Bzl) | FAB | 1100 |

TABLE 1-continued

| Ex. | X | Y | Z | Physico-chemical Data | MH+ | |
|---|---|---|---|---|---|---|
| 16 | id. | Phe | Thr(Bzl) | E.S. | 999.6 | |
| 17 | id. | Phe | Glu(Bzl) | E.S. | 1027.7 | |
| 18 | 4-(N[CH$_3$]$_2$—C$_2$H$_4$—NH—CO—O—)Pro | Phe | Tyr(Bzl) | FAB | 1089 | |
| 19 | 4-(NH—C$_2$H$_4$—NH—CO—O—)Pro, COCH$_3$ | Phe | Tyr(Bzl) | E.S. | 1103.6 | |
| 20 | NH$_2$—C$_2$H$_4$—CO—O—NCH$_3$Ser | Tyr | Tyr(Bzl) | E.S. | 1065.6 | |
| 21 | MeSer | Phe | Tyr(Bzl) | FAB | 963 | 1) |
| 22 | 4-(pyridyl-C$_2$H$_4$—NH—CO—O)Pro | Phe | Tyr(Bzl) | FAB | 1123 | 2) |
| 23 | 4-(NH$_2$—C$_5$H$_{10}$—NH—CO—O—)Pro | Phe | Tyr(Bzl) | FAB | 1118 | 3) |
| 24 | 4-HyPro | His | Tyr(Bzl) | E.S. | 965.7 | |
| 25 | id. | Tyr | Glu(Bzl) | FAB | 941 | |
| 26 | id. | Phe | Thr(Bzl) | FAB | 913 | |
| 27 | 4-NH$_2$-Pro | Phe | Tyr(Bzl) | FAB | 974 | 4) |
| 28 | N$^\alpha$-Me-Lys | Phe | Tyr(Bzl) | FAB | 967 | |
| 29* | 4-(NH$_2$—C(NH)—NH—C$_2$H$_4$—NH—CO—O)Pro | Tyr | Tyr(Bzl) | E.S. | 1118.7 | |
| 30 | 4-(NH$_2$—C$_2$H$_4$—NH—CO—O—)Pro | Tyr | Thr(Bzl) | E.S. | 1015.5 | |
| 31 | 4-(NH$_2$—C$_2$H$_4$—NH—CO—O)Pro | Phe | Ser(Bzl) | E.S. | 985.1 | |
| 32 | 4-(NH$_2$—C$_2$H$_4$—NH—CO—O)Pro (cis) | Phe | Ser(Bzl) | E.S. | 985.1 | |
| 33 | 4-(NH$_2$—C$_2$H$_4$—NH—CO—O)Pro | Ser | Thr(Bzl) | E.S. | 939.0 | |
| 34 | 4-(NH$_2$—C$_2$H$_4$—NH—CO—O)Pro | Thr | Thr(Bzl) | E.S. | 953.1 | |
| 35 | 4-NH$_2$-Pro- | Phe | Ser(Bzl) | E.S. | 898.0 | |
| 36 | 4-[N(CH$_3$)$_2$—C$_2$H$_4$—NH—CO—O]Pro | Phe | Ser(Bzl) | E.S. | 1013.2 | |
| 37 | 4-(NH$_2$—C$_2$H$_4$—NH—CO—O)Pro | Tyr | Ser(Bzl) | | | |
| 38 | 4-NH$_2$-Pro (cis) | Phe | Ser(Bzl) | E.S. | 898 | |
| 39 | 4-(NH$_2$—C$_2$H$_4$—NH—CO—O)Pro | Ile | Thr(Bzl) | | | |
| 40 | 4-(NH$_2$—C$_2$H$_4$—NH—CO—O)Pro | Phe | Cys(Bzl) | | | |

1) $[\alpha]^D_{22} = -47.0°$ (95% AcOH; c = 0.1)
2) $[\alpha]^D_{22} = -54.0°$ (95% AcOH; c = 0.1)
3) $[\alpha]^D_{22} = -54.0°$ (95% AcOH; c = 0.1)
4) $[\alpha]^D_{22} = -99°$ (95% AcOH; c = 0.1)
id. = idem
*The peptide of Example 29 may be prepared as follows:

The protected peptide cyclo[(NH$_2$—C(=NH)—NH—C$_2$H$_4$—NH—CO—O—)]-Pro-Tyr-DTrp-Lys(Dde)-Tyr(Bzl)-Phe is assembled on the resin using Fmoc solid phase synthesis procedure as described in Example 2. Instead of N$^\epsilon$-Boc-Lys, N$^\epsilon$-Dde-Lys is used to preferentially introduce the guanidinyl function on the basic side chain of the HyPro residue. After assembling the peptide the terminal Fmoc group is removed and the peptide cyclized and finally deprotected as in Example 2. This peptide is dissolved in DMF and diisopropyl ethyl amine (3 eq) and HOBt (4 eq) are added followed by 3,5-dimethyl-pyrazolylformamidinium nitrate (4 eq) and the solution is stirred for 72 h. at RT. The reaction mixture is evaporated in vacuo and then subjected to treatment with anhydrous hydrazine (2% in DMF) for 30 min to remove the Dde group on Lys. The crude title peptide (Example 29) is then purified by HPLC in acetonitrile and aqueous triethylammonium phosphate system.

EXAMPLE 41

Cyclo[4-(NH$_2$—C$_2$H$_4$—NH—CO—O—)Pro-Ala-DTrp-Lys-Tyr(3-Bzl)-Phe]

MH+ (E.S.): 984.5

EXAMPLE 42

Cyclo[{4-(NH$_2$—C$_2$H$_4$—NH—CO—O—)Pro}-(p-NH$_2$)-Phe-DTrp-Lys-Tyr(3-Bzl)-Phe]

MH+ (E.S.): 1076.6

EXAMPLE 43 cyclo[4-HyPro-Phe-DTrp-Lys-Tyr(Bzl)-βNal]

MH+ (E.S.): 1025.5

EXAMPLE 44

Cyclo[4-HyPro-Phe-DTrp-Lys-Tyr(Bzl)-Tyr]

MH+ (E.S.): 991.6

EXAMPLE 45

Cyclo[MePhe-His-DTrp-Lys-Tyr(Bzl)-Dab]

MH+ (FAB): 1005

EXAMPLE 46

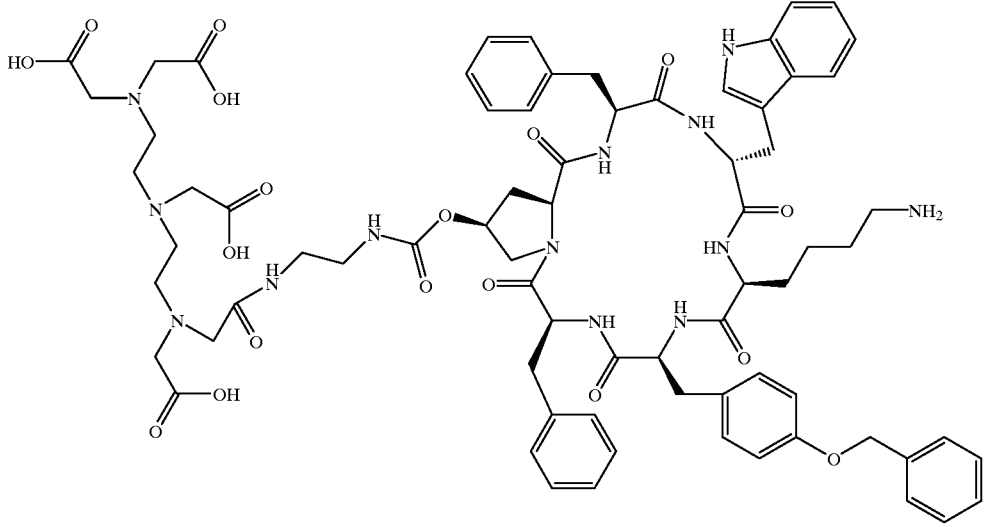

a) cyclo[4-(NH₂—C₂H₄—NH—CO—O—)Pro-Phe-DTrp-Lys(ε-Boc)-Tyr(Bzl)-Phe]

60 mg cyclo[4-NH₂—C₂H₄—NH—CO—O)Pro-DTrp-Lys-Tyr(Bzl)-Phe], 12 mg NaHCO₃ and 12 mg (BOC)₂O are dissolved in 10 ml DMF/water 7/3 and kept at room temperature with stirring overnight. After evaporation of the solvent the title product is isolated by silica gel chromatography using methylene chloride/methanol/acetic acid₅₀% 8/2/0.25 as mobile phase.

b) cyclo[4-(DTPA-NH—C₂H₄—NH—CO—O—)Pro-Phe-DTrp-Lys(ε-Boc)-Tyr(Bzl)-Phe]

120 mg DTPA-hydrazide are dissolved in 5 ml DMF and adjusted to pH 3 with drops of diethyl ether/3N HCl. After cooling down to −15° 4 μl tert.-butylnitrite and a solution of 15 mg of the compound obtained in a) above in 3 ml DMF containing 15 μl Hünig base is added. After 4 hours the solvent is removed by evaporation and the remaining residue is deprotected without any further purification.

c) cyclo[4-(DTPA-NH—C₂H₄—NH—CO—O—)Pro-Phe-DTrp-Lys-Tyr(Bzl)-Phe]

The crude product of step b) is treated with 5 ml TFA/water 95/5 at 0° for 10 minutes. After diluting with 50 ml water the solution is directly transferred on a RP18-HPLC column and eluted with a water/acetonitrile/TFk₀.₁% gradient. Pure fractions are pooled and lyophilized. FAB-MS: 1436.6

EXAMPLE 47

¹¹¹In Labeled Compound of Example 46c)

1 mg of the compound of Example 46c) is dissolved in 5 ml 0.01 M acetic acid. The resulting solution is passed through a 0.22μ Millex®-GV filter (Registered Trade Mark) and dispensed in 0.1 ml portions and stored at −20°. ¹¹¹InCl₃ (Amersham, 1 mCi/100 μl) is prediluted in an equal volume of 0.5 M sodium acetate and labeling is carried out by mixing the ligand with the InCl₃ solution and gentle homogenization at room temperature.

HEPES buffer, pH 7.4, is then added to make a solution 10⁻⁶ M.

EXAMPLE 48

Cyclo-[4-(DOTA-NH—C₂H₄—NH—CO—O)Pro-Phe-DTrp-Lys-Ser(Bzl)-Phe]

M.S.: 1371.57

This compound is labelled with ⁹⁰Y as follows: 20 μl of ⁹⁰Y(1.2 mCi, 0.04 M HCl) to 20 μl of 50 μM of above compound (0.15 M NH₄=Ac, 0.3% BSA, pH 4.5). This solution is incubated at 100° for 15 minutes. An aliquot is removed and diluted with 4mM DTPA (pH 4.5) before being analyzed by C18 reverse phase HPLC to ascertain the amount of free unchelated ⁹⁰Y in the reaction mixture (as indicated by the (as indicated by the presence of [⁹⁰YDTPA]²⁻.

EXAMPLE 49

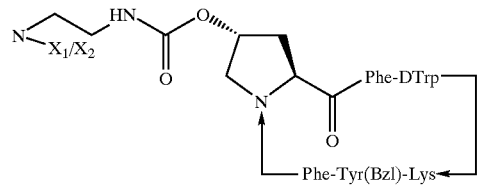

116 mg of the compound of Example 46a), 12 mg NaCNBH₃ and 2 equivalents of the respective aldehyde are dissolved in 25 ml DMF/HOAc₁% and kept at 60° until no starting material can be detected by TLC. After removal of the solvent the remaining residue is purified by silica gel chromatography (methylene chloride/methanol/HOAc₅₀% 9/1/0.125→8/2/0.25) in order to separate mono- and double-alkylated end product.

--- i) Aldehyde: (D)-glucose
   X₁ = HOCH₂—(CHOH)₄—CH₂—   X₂ = H
   E.S.-MH⁺ = 1225.4 ii) Aldehyde: (D)-glucose
    X₁ = X₂ = HOCH₂—(CHOH)₄—CH₂—
    E.S.-MH⁺ = 1389.6 iii) Aldehyde: 2,3-O-isopropylidene-(D)-glyceraldehyde
     X₁ = HOCH₂—CHOH—CH₂—   X₂ = H iv) Aldehyde: 2,3-O-isopropylidene-(D)-glyceraldehyde
    X₁ = X₂ = HOCH₂—CHOH—CH₂—

-continued

E.S.-MH$^+$ = 1209.4 v) Aldehyde: hydroxyacetaldehyde
$X_1 = X_2 = HOCH_2—CH_2—$
E.S.-MH$^+$ = 1149.4

The COMPOUNDS OF THE INVENTION in free form or in the form of pharmaceutically acceptable salts and complexes exhibit valuable pharmacological properties as indicated in in vitro and in vivo tests and are therefore indicated for therapy.

In particular, the COMPOUNDS OF THE INVENTION bind to at least one somatostatin receptor subtype. 5 somatostatin receptor subtypes, SST-1, SST-2, SST-3, SST-4 and SST-5 have been cloned and characterized.

hSST-1, hSST-2 and hSST-3 and their sequences have been disclosed by Y. Yamada et al. in Proc. Nat. Acad. Sci., 89, 251–255 (1992). hSST-4 and its sequence have been disclosed by L. Rohrer et al. in Proc. Acad. Sci., 90, 4196–4200 (1993). hSST-5 and its sequence have been described by R. Panetta et al. in Mol. Pharmacol. 45, 417–427, 1993.

The binding assays may be carried out as disclosed hereunder using membranes prepared from hSST-1, hSST-2, hSST-3, hSST-4 or hSST-5 selective cell lines, e.g. CHO cells stably expressing hSST-1, hSST-2, hSST-3, hSST-4 or hSST-5.

Brain or pituitary tissue is used in which hSST are visualized with e.g. in situ hybridization and/or receptor autoradiography. Membranes are prepared according to known methods, e.g. as disclosed by J C. Reubi et al. in J. Clin. Endocrinol. Metab. 1987, 65, 1127–1137. Membranes prepared from hSST selective cell lines, e.g. CHO cells stably expressing hSST-1 or hSST-2 or hSST-3 or hSST-4 or hSST-5 are incubated in triplicate in a total volume of 300 $\mu$l at 22° C. for 30 min with increasing concentrations of [$^{125}$I-Tyr$^3$]-octreotide in 10 mmol/l Hepes buffer (pH 7.6) containing 0.5% BSA. The incubation is terminated by rapid filtration through Whatman GF/B glass fiber filters, which are then washed four times each with 5 ml ice cold 10 mmol/l Tris/150 mmol/l NaCl. The filters are counted in a LKB counter at 78% counting efficiency. Specific binding is total binding minus non-specific binding in the presence of 1 $\mu$mol/l somatostatin-14. The experiments are carried out in triplicate. The affinity constant ($K_D$) and number of binding sites are calculated from Scatchard plots of the data.

The COMPOUNDS OF THE INVENTION, e.g. as indicated above, respectively, have in the above binding assays towards hsST-1, hSST-2, hSST-3, hSST-4 and/or hSST-5 an IC$_{50}$ in the nMolar range, preferably an IC$_{50}$ of from 0.1 to 10 nM (IC$_{50}$=concentration for half-maximal inhibition in a competition binding assay using [$^{125}$I-Tyr$^3$]-octreotide the same radioligand as indicated above).

| | IC$_{50}$ (nM) | | | | |
|---|---|---|---|---|---|
| Compound | hSSTR-1 | hSSTR-2 | hSSTR-3 | hSSTR-4 | hSSTR-5 |
| Ex. 1 | 63.00 | 0.94 | 1.90 | 320.00 | 0.35 |
| Ex. 2 | 4.60 | 2.30 | 0.93 | 490.00 | 0.46 |
| Ex. 14 | 7.40 | 1.20 | 0.86 | >100 | 0.13 |
| Ex. 31 | 0.50 | 0.80 | 3.90 | 3.60 | 2.90 |

-continued

| | IC$_{50}$ (nM) | | | | |
|---|---|---|---|---|---|
| Compound | hSSTR-1 | hSSTR-2 | hSSTR-3 | hSSTR-4 | hSSTR-5 |
| Ex. 32 | 3.80 | 0.13 | 57.00 | 7.90 | 2.00 |
| Ex. 36 | 0.60 | 1.30 | 2.40 | 2.20 | 4.50 |

Furthermore, the COMPOUNDS OF THE INVENTION show GH-release inhibiting activity as indicated by the inhibition of GH release in vitro from cultured pituitary cells. Anterior pituitary glands from adult male rats are cut into small pieces and dispersed using 0.1% trypsin in 20 mM HEPES buffer. The dispersed cells are cultured for four days in MEM (Gibco) supplemented with 5% fetal calf serum, 5% horse serum, 1 mM NaHCO$_3$, 2.5 nM dexamethasone, 2.5 mg/ml insulin and 20 U/ml Pen/Strep. On the day of the experiment the attached cells are washed two times with Krebs-Ringer medium buffered with 20 mM HEPES and supplemented with 5 mM glucose and 0.2% BSA. Subsequently the cells are incubated for two to four hours with the test compound in the presence of 3×10$^{-10}$ M growth hormone releasing factor. The amount of growth hormone released into the medium is measured by RIA. COMPOUNDS OF THE INVENTION inhibit the release of GH concentration-dependent from 10$^{-11}$ to 10$^{-6}$ M. Compound of Example 2 has an IC$_{50}$ of 0.4 nM.

COMPOUNDS OF THE INVENTION also inhibit the release of insulin and/or glucagon, as indicated in standard tests using male rats. The test-substance is administered at varying, logarithmically staggered doses employing at least 5 rats per dose. 1 hour after s.c. administration of the test substance blood is taken. The determination of the blood serum insulin and glucagon levels is effected by radio-immuno-assay. COMPOUNDS OF THE INVENTION are active in this test when administered at a dosage in the range of from 0.02 to 1000, e.g. to 10, $\mu$g/kg s.c. Compound of Example 9 has an EC$_{50}$ of 1.8 $\mu$g/kg s.c. with respect to insulin secretion.

The COMPOUNDS OF THE INVENTION are accordingly useful for the treatment of disorders with an aetiology comprising or associated with excess GH-secretion, e.g. in the treatment of acromegaly as well as in the treatment of diabetes mellitus, especially complications thereof, e.g.angiophathy, proliferative retinopathy, dawn phenomenon and nephropathy and other metabolic disorders related to insulin or glucagon release.

The COMPOUNDS OF THE INVENTION also inhibit gastric acid secretion, exocrine and endocrine pancreatic secretion and the secretion of various peptides of the gastrointestinal tract, as indicated in standard tests using e.g. rats with gastric or pancreatic fistulae, wherein the compounds are active at a dose from 0.01 to 10 mg/kg.

The COMPOUNDS OF THE INVENTION additionally are thus useful for the treatment of gastro-intestinal disorders, for example in the treatment of peptic ulcers, enterocutaneous and pancreaticocutaneous fistula, irritable bowel syndrome and disease, dumping syndrome, watery diarrhea syndrome, AIDS-related diarrhea, chemotherapy-induced diarrhea, acute or chronic pancreatitis and gastrointestinal hormone secreting tumors (e.g. vipomas, glucagonomas, insulinomas, carcinoids and the like) as well as gastrointestinal bleeding.

The COMPOUNDS OF THE INVENTION are also effective in the treatment of tumors which are somatostatin receptor positive, particularly tumors bearing hSST-1, hSST- 2, hSST-3, hSST-4 and/or hSST-5, as indicated in proliferation tests with various cancer cell lines bearing such somatostatin receptors.

The AR42J rat pancreatic tumor cell line is derived from an azaserine-induced exocrine pancreatic tumor (Jessop and Hay, 1980). The absence of mycoplasma is regularly checked using bisbenzimide staining and the GenProbe hybridization assay (San Diego, Calif.). Cultures are propagated in DMEM supplemented with 10% fetal calf serum (FCS) at 5% $CO_2$. Cells are grown in the absence of antibiotics or antifungal agents. Subconfluent AR42J cells are trypsinized, diluted in DMEM +2.5% FCS and seeded in uncoated 96-well plates. After a 48-hr incubation period (Day 0), the number of cells in a separate control plate is determined both by counting cells in a Coulter counter and by the SRB calorimetric assay. The cells are then exposed to the compound to be tested for 2 to 5 days at various concentrations and then counted. Under these conditions COMPOUNDS OF THE INVENTION inhibit the proliferation of the tumor cells at a concentration of from $10^{-12}$ to $10^{-6}$ M. Compound of Example 2 has an $IC_{50}$ of 0.7±0.3 (SE) nM.

Tumor Growth Studies in vivo

Female nude mice (nu/nu Balbc-A from IFFA Credo, Lyon, France) weighing 19–22 g, are kept in groups of 5 animals in macrolon cages (type III, 16×22×11 cm). The cages are placed in ventilated cabinets (Iffa Credo) that are maintained at 24±1° C. The animals have free access to drinking water and a pathogen-free rodent diet (Diet A, Kliba, Basel, Switzerland). To initiate tumors from cultured cells, AR42J cells are trypsinized and 5–10×10$^6$ tumor cells (in 0.2 ml) are injected subcutaneously (s.c.) into both flanks of nude mice. Treatment commences 2–4 days following inoculation of the tumor cells, the compound to be tested being preferably administered as a continuous infusion, e.g. at a rate of 10 to 50 μg/kg/hr. The size of the tumors is determined with a caliper. To calculate the tumor volume the equation "volume (ellipsoid)=length×depth×height×0.52" is used. For statistical calculations Student's t-test is applied. In this assay compound of Example 2 inhibits tumor growth at day 11 by 51% vs saline control.

The COMPOUNDS OF THE INVENTION are thus useful for the treatment of malignant cell proliferative diseases, e.g. cancer tumors, particularly tumors bearing the somatostatin receptor types targeted by the COMPOUNDS, e.g. as disclosed hereunder for the chelated COMPOUNDS.

The COMPOUNDS OF THE INVENTION also have an inhibiting effect on angiogenesis, as indicated in standard tests, e.g. in nude mice as disclosed below.

Mice are anesthetized by 400 mg/kg chloral hydrate (Sigma) i.p. Tumor cells (0.1 to 10×10$^6$ in 0.1 ml) (SiHa cells and MDA-MB-231 cells prepared as disclosed in Angiogenesis, Ed. by R. Steiner, P. B. Weisz and R. Langer, 1992, Switzerland) are inoculated intracutaneously. Usually two midventral sites/mouse are injected which are located distant from the main ventral skin vessels so that the background vessel count is low. Control groups receive 0.1 ml 0.02% trypan blue in PBS. 10 days following injection, anesthetized mice are sacrificed by $CO_2$ inhalation. The skin is mounted onto a plastic ring (40 mm diameter) for evaluation by an inverted microscope (Zeiss IM) at 12.5- and 25-fold magnification. As a measure of angiogenesis, vessels are photographed and those are counted that are directly connected with the tumor. In control animals those vessels are counted that are connected to a defined area around the injection site. This area corresponds to the mean area of the dermal tumors. The latter is determined by use of a caliper according to the equation $3.14 \times r^2$. The compounds to be tested are administered s.c. either on the day of tumor inoculation or 3 days later. Control animals are vehicle-treated. In this assay, COMPOUNDS OF THE INVENTION inhibit blood vessel formation when administered at a dose of e.g. 0.01 to 1000 μg/kg s.c.

The COMPOUNDS OF THE INVENTION additionally are thus useful for the prevention or treatment of angiogenesis, inflammatory disorders and retinopathy.

The COMPOUNDS OF THE INVENTION also have an inhibiting effect on the proliferation and migration of smooth muscle cells as indicated in following tests.

Chronic Alloaraft Rejection

COMPOUNDS OF THE INVENTION inhibit chronic rejection of a rat kidney allograft. The kidney of a male DA (RT1$^a$) rat is orthotopically transplanted into a male Lewis (RT1$^1$) recipient. In total 24 animals are transplanted. All animals are treated with cyclosporine A at 7.5 mg/kg/day per os for 14 days starting on the day of transplantation, to prevent acute cellular rejection. Contralateral nephrectomy is not performed. Each experimental group treated with a distinct dose of a COMPOUND OF THE INVENTION or placebo comprises six animals. Starting at day 53–64 after transplantation, the recipient animals are treated for another 69–72 days by infusion with a COMPOUND OF THE INVENTION or receive placebo. At 14 days after transplantation organ perfusion is measured by MRI. This is repeated at days 53–64 after transplantation and at the end of the experiment. The animals are then autopsied. Administration of a COMPOUND OF THE INVENTION e.g compound of Example 31, at a dose of 1 to 10 μg/kg/h in this rat kidney allograft model yields an improved organ perfusion. A sharp drop of IGF-1 levels has also been measured.

Angioplasty

Studies on angioplasty are done in the model of Balloon catheter injury: Balloon catheterization is performed on day 0, essentially as described by Powell et al. (1989). Under Isofluorane anesthesia, a Fogarty 2F catheter is introduced into the left common carotid artery via the external carotid and inflated (distension ≈10 μl $H_2O$). The inflated balloon is withdrawn along the length of the common carotid three times, the latter two times whilst twisting gently to obtain a uniform de-endothelialization. The cathether is then removed, a ligature placed around the external carotid to prevent bleeding and the animals allowed to recover.

2 groups of 12 RoRo rats (400 g, approximately 24 weeks old) are used for the study: one control group and one group receiving a COMPOUND OF THE INVENTION. The rats are fully randomized during all handling, experimental procedures and analysis.

The compound to be tested is administered by continuous infusion using minipumps at a rate of 10–50 μg/kg/h starting 3 days before balloon injury (day −3) until the end of the study, 14 days after balloon injury (day +14). Rats are kept in individual cages and allowed food and water ad libitum.

The rats are then anesthetized with Isofluorane, a perfusion catheter inserted through the left ventricle and secured in the aortic arch, and an aspiration cannula inserted into the right ventricle. Animals are perfused under a perfusion pressure of 150 mmHg, firstly for 1 min. with 0.1 M phosphate buffered saline solution (PBS, pH 7.4) and then for 15 min. with 2.5% glutaraldehyde in phosphate buffer (pH 7.4). Carotid arteries are then excised, separated from surrounding tissue and immersed in 0.1 M cacodylate buffer (pH 7.4) containing 7% saccharose and incubated overnight at 4° C. The following day the carotids are immersed and shaken for 1 h at room temperature in 0.05% $KM_4O$. in 0.1

M cacodylate. The tissues are then dehydrated in a graded ethanol series; 2×10 min in 75%, 2×10 min in 85%, 3×10 min in 95% and 3×10 min in 100% ethanol. The dehydrated carotids are then embedded in Technovit 7100 according to the manufacturers recommendation. The embedding medium is left to polymerize overnight in an exsiccator under argon. Sections 4 µm thick are cut from the middle section of each carotid with a hard metal knife on a rotary microtome and stained for 2 min with Giemse-stain. About 5 sections from each carotid are thus prepared and the cross-sectional area of the media, neointima and the lumen morphometrically evaluated by means of an image analysis system (MCID, Toronto, Canada).

In this assay, the COMPOUNDS OF THE INVENTION inhibit myointimal proliferation when administered by continuous infusion at a daily dose of from 0.2 to 10 mg/kg, preferably 0.05 to 5 mg/kg.

The COMPOUNDS OF THE INVENTION are thus also useful for preventing or combating graft vessel diseases, e.g. allo- or xenotransplant vasculopathies,e.g. graft vessel atherosclerosis, e.g. in a transplant of organ, e.g. heart, lung, combined heart-lung, liver, kidney or pancreatic transplants, or for prev enting or treating restenosis and/or vascular occlusion following vascular injury, e.g. angioplasty.

For all the above indications the required dosage will of course vary depending upon, for example, the COMPOUND OF THE INVENTION employed, the host, the mode of administration and the severity of the condition to be treated. In general however satisfactory results are obtained on administration on the order of from 1 µg to 0.5 mg/kg/day of COMPOUND. An indicated daily dosage for patients is in the range from about 2 µg to about 20 mg, preferably about 0.01 to about 20 mg, e.g. about 10 to about 5000 µg s.c. of the compound conveniently administered in divided doses up to 3 times a day in unit dosage form containing for example from about 0.5 µg to about 10 mg, e.g. from about 2 µg to 10 mg, of the COMPOUND or in sustained release form.

The COMPOUNDS OF THE INVENTION may be administered in free form or in pharmaceutically acceptable salt form or complexes. Such salts and complexes may be prepared in conventional manner and exhibit the same order of activity as the free compounds. The present invention also provides a pharmaceutical composition comprising a COMPOUND OF THE INVENTION, e.g. a compound of formula II, in free base form or in pharmaceutically acceptable salt form or complex form in association with a pharmaceutically acceptable diluent or carrier. such compositions may be formulated in conventional manner. The COMPOUNDS OF THE INVENTION or a pharmaceutically acceptable salt or complex thereof may be administered by any conventional route, for example parenterally e.g. in form of injectable solutions or suspensions, or in a nasal or a suppository form.

In accordance with the foregoing the present invention further provides:

a) a COMPOUND OF THE INVENTION e.g. a compound of formula II, or a pharmaceutically acceptable salt or complex thereof for use as a pharmaceutical;

b) a method of preventing or treating disorders as indicated above in a subject in need of such treatment, which method comprises administering to said subject an effective amount of a COMPOUND OF THE INVENTION, e.g. a compound of formula II or a pharmaceutically acceptable salt or complex thereof; or c) a COMPOUND OF THE INVENTION or a pharmaceutically acceptable salt or complex thereof for use in the preparation of a pharmaceutical composition for use in any method as defined under b above.

The chelated COMPOUNDS OF THE INVENTION or a pharmaceutically acceptable salt thereof are useful either as an imaging agent, e.g. visualization of somatostatin receptor positive tissues and cells e.g. somatostatin receptor positive tumors and metastases, inflammatory or autoimmume disorders exhibiting somatostatin receptors, tuberculosis or organ rejection after transplantation, when complexed with a γ- or positron-emitting nuclide, e.g. $^{111}$In, $^{161}$Tb or $^{86}$Y, or as a radiopharmaceutical for the treatment in vivo of somatostatin receptor positive tumors and metastases, rheumatoid arthritis and severe inflammation conditions when complexed with an α- or β-emitting nuclide, or a nuclide with Auger-e$^-$-cascades, e.g. $^{90}$Y, $^{61}$Tb $^{211}$At, $^{213}$Bi or $^{201}$Tl as indicated by standard tests.

In particular, it is observed that the chelated COMPOUNDS OF THE INVENTION e.g. $^{111}$In, $^{88}$Y $^{90}$Y, $^{153}$Sm, $^{186}$Re or $^{161}$Tb chelated COMPOUNDS OF THE INVENTION bind with a good affinity to somatostatin receptors with pKi values of from about 8 to 10. Compound of Example 47 has an IC$_{50}$ value of 1.2 nM towards hSST-2, 0.65 nM towards hSST-3 and 0.30 nM towards hSST-5.

The affinity of the chelated COMPOUNDS OF THE INVENTION and their complexes for somatostatin receptors can also be shown by in vivo testing, according to standard test methods, e.g. as disclosed in GB-A-2,225,579. For example the compound of Example 47 gives a significant tumor accumulation 4 hours after injection into mice or rats bearing exocrine pancreatic tumor bearing SST-2 receptors.

After administration of a chelated COMPOUND OF THE INVENTION in complexed form, e.g. a $^{111}$In, $^{86}$Y or $^{161}$Tb chelated compound at a dosage of from 1 to 5 µg/kg labelled with 0.1 to 5 mCi radionuclide, preferably 0.1 to 2 mCi the tumor site becomes detectable together with the organs where excretion essentially takes place.

The chelated COMPOUNDS OF THE INVENTION when radiolabelled with an α- or β-emitting radionuclide or a nuclide with Auger-e$^-$-cascades have an antiproliferative and/or cytotoxic effect on tumor cells bearing somatostatin receptors, e.g. as indicated in nude mice tests.

Nude mice are inoculated with AR42J rat pancreatic tumor cells or NCI-H69 human small cell lung cancer as disclosed above. When tumors have reached a volume of 1 to 2 cm$^3$ animals are randomized into control and treatment groups. Control animals, receive either an unlabelled COMPOUND or a chelated COMPOUND in complexed form by i.p. or i.v. injections at doses corresponding to the highest dose of the treatment groups. Doses up to 40 mCi/kg are given per mouse. The size of the tumors is determined with a caliper as disclosed above. For statistical calculations Student's t-test is applied. In this test, transient tumor shrinkage to 50% of initial is observed after one week and tumor growth is delayed for two weeks upon a single application of the compound of Example 48. In contrast the control groups showed continuous tumor growth with a volume doubling time of about seven days.

Accordingly, in a series of specific or alternative embodiments, the present invention also provides:

1. Use of a chelated COMPOUND OF THE INVENTION, e.g. a chelated compound of formula II, in complexed form for in vivo detection of somatostatin receptor positive cells and tissues in a subject and recording the localization of the receptors targeted by said chelate.

The radiolabelled COMPOUNDS OF THE INVENTION for use as an imaging agent may be administered intraperitoneally, preferably intravenously, e.g. in the form of injectable solutions or suspensions, preferably in a single injection. The radiolabelling may preferably be performed shortly before administration to a subject.

A chelated COMPOUND OF THE INVENTION may advantageously be administered in a dose comprising 0.2 to 20 mCi of a stably complexed nuclide, preferably 1 to 10 mCi.

In animals an indicated dosage range may be of from 0.01 to 1 μg/kg of a chelated COMPOUND OF THE INVENTION complexed with 0.02 to 0.5 mCi γ-emitting radionuclide. In larger mammals, for example humans, an indicated dosage range may be of from 1 to 20 μg chelated COMPOUND complexed e.g. with 1 to 10 mCi $^{111}$In or $^{86}$Y.

2. Use of a chelated COMPOUND OF THE INVENTION e.g. a chelated compound of formula II, in complexed form for in vivo treatment of somatostatin receptor positive tumors and metastases.

Dosages employed in practicing the radiotherapeutic use of the present invention will of course vary depending e.g. on the particular condition to be treated, for example the known radiotoxicity to normal organs expressing SST-2 receptors, the volume of the tumor and the therapy desired. In general, the dose is calculated on the basis of pharmacokinetic and radioactivity distribution to healthy organs and on observed target uptake. A β-emitting complex of a chelated COMPOUND may be administered repeatedly e.g. over a period of 1 to 3 months.

In animals an indicated dosage range may be of from 20 to 100 μg/kg chelated COMPOUND complexed with 15 to 70 mCi $^{90}$Y or $^{161}$Tb.

The chelated COMPOUNDS OF THE INVENTION in complexed form may be administered by any conventional route, in particular intraperitoneally or intravenously, e.g. in the form of injectable solutions or suspensions. They may also be administered advantageously by infusion, e.g. an infusion of 30 to 60 min. Depending on the site of the tumor, they may be administered as close as possible to the tumor site, e.g. by means of a catheter.

The chelated COMPOUNDS OF THE INVENTION in complexed form may be suitable for imaging or treating tumors such as pituitary, gastro-enteropancreatic, carcinoids, central nervous system, breast, prostatic, ovarian or colonic tumors, small cell lung cancer, paragangliomas, kidney cancer, skin cancer, neuroblastomas, pheochromocytomas, medullary thyroid carcinomas, myelomas, lymphomas, Hodgkins and non-Hodgkins disease, bone tumors and metastases thereof, and rheumatoid arthritis.

According to a further aspect of the invention, there is provided a pharmaceutical composition comprising a chelated COMPOUND OF THE INVENTION in free or complexed form together with one or more pharmaceutically acceptable carriers or diluents therefor. Such compositions may be manufactured in conventional manner and may be presented, e.g. for imaging, in the form of a kit comprising two separate dosages, one being the radionuclide and the other the un complexed chelate, with instructions for mixing them. For radiotherapy, the chelated COMPOUNDS OF THE INVENTION in free or completed form may preferably be presented as a hot liquid formulation.

What is claimed is:

1. A somatostatin analogue which is a hexapeptide unit numbered from 1 to 6, the residues at positions 3 through 6 of said hexapeptide unit having the sequence of formula I -(D/L)Trp-Lys-X$_1$-X$_2$-     (1)

wherein X$_1$ is a radical of formula (a) or (b)

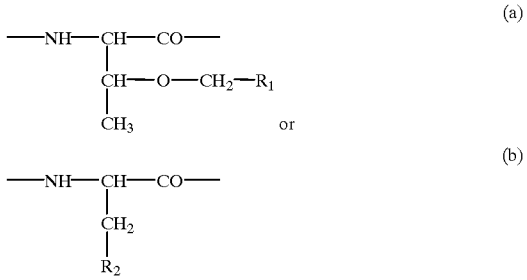

wherein R$_1$ is optionally substituted phenyl,
R$_2$ is —Z$_1$CH$_2$—R$_1$, —CH$_2$—CO—O—CH$_2$—R$_1$,

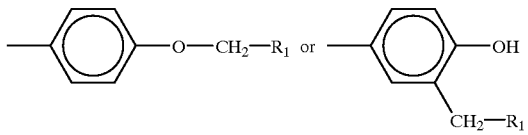

wherein Z$_1$ is O or S, and

X$_2$ is an α-amino acid having an aromatic residue on the C$_\alpha$ side chain, or an amino acid unit selected from Dab, Dpr, Dpm, His, (Bzl)HyPro, thienyl-Ala, cyclohexyl-Ala and t.-butyl-Ala, the residue Lys of said sequence corresponding to the residue Lys$^9$ of the native somatostatin-14, or a chelate thereof, in free form or in salt or complex form.

2. A somatostatin analogue according to claim 1 in which the hexapeptide unit is cyclic with a direct peptide linkage between the α-carbonyl group of the residue at position 6 and the α-amino group of the residue at position 1, or a chelate thereof, in free form or in salt or complex form.

3. A somatostatin analogue according to claim 1 which is a compound of formula (II)

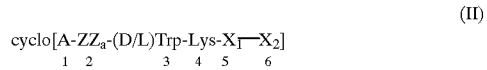

wherein

X$_1$ and X$_2$ are as in claim 1,

A is a divalent residue selected from the group consisting of Pro,

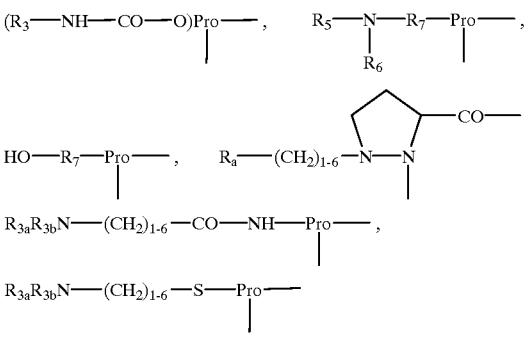

-continued

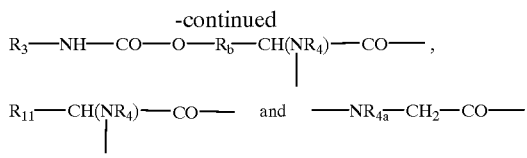

wherein $R_3$ is $NR_8R_9$-$C_{2-6}$alkylene, guanidino-$C_{2-6}$alkylene or $C_{2-6}$alkylene-COOH, $R_{3a}$ is H, $C_{1-4}$alkyl or has independently one of the significances given for $R_3$, $R_{3b}$ is H or $C_{1-4}$alkyl, $R_a$ is OH or $NR_5R_6$, $R_b$ is —$(CH_2)_{1-3}$— or —$CH(CH_3)$—, $R_4$ is H or $CH_3$, $R_{4a}$ is optionally ring-substituted benzyl, each of $R_5$ and $R_6$ independently is H, $C_{1-4}$alkyl, ω-amino-$C_{1-4}$alkylene, ω-hydroxy-$C_{1-4}$alkylene or acyl, $R_7$ is a direct bond or $C_{1-6}$alkylene, each of $R_8$ and $R_9$ independently is H, $C_{1-4}$alkyl, ω-hydroxy-$C_{2-4}$alkylene, acyl or $CH_2OH$—$(CHOH)_c$—$CH_2$— wherein c is 0, 1, 2, 3 or 4, or $R_8$ and $R_9$ form together with the nitrogen atom to which they are attached a heterocyclic group which may comprise a further heteroatom, and $R_{11}$ is optionally ring-substituted benzyl, —$(CH_2)_{1-3}$—OH, $CH_3$—CH(OH)— or —$(CH_2)_{1-5}$—$NR_5R_6$, and $ZZ_a$ is a natural or unnatural α-amino acid unit, or a chelate thereof, in free form or in salt or complex form.

4. A somatostatin analogue according to claim 1 wherein A comprises an amino group bearing a chelating group, in free form, in salt form or complexed with a detectable element.

5. A process for the production of a somatostatin analogue according to claim 1 comprising
   a) removing at least one protecting group which is present in a somatostatin analogue comprising a residue of formula I, the somatostatin analogue being in protected form, or
   b) linking together by an amide bond two peptide units, each of them containing at least one amino acid in protected or unprotected form, wherein the amide bond is in such a way that the desired amino acid sequence is obtained and, where required, effecting process step a), or
   c) removing a functional group of an unprotected or a protected somatostatin peptide or converting it into another functional group so that another unprotected or protected peptide is obtained and in the latter case stage a) of the process is effected, or
   d) to produce a chelated somatostatin analogue linking together a chelating agent and a non-chelated somatostatin analogue in protected or unprotected form and comprising a free amino group in such a way that the chelating group is fixed on the desired amino group of the somatostatin analogue, and stage a) is then optionally effected and recovering the somatostatin analogue thus obtained in free form, in salt form or optionally complexed with a detectable element.

6. A pharmaceutical composition comprising a pharmaceutical acceptable carrier or diluent and a therapeutically effective amount of a somatastatin analogue according to claim 1 or a chelate thereof, or a pharmaceutically acceptable salt or a complex with a detectable element.

7. A method of treating disorders with an aetiology comprising or associated with excess GH-secretion, gastrointestinal disorders, malignant cell proliferative diseases, angiogenesis, or of preventing or combating graft vessel diseases, restenosis and vascular occlusion following vascular injury, which method comprises administering to a subject in need of such treatment a therapeutically effective amount of a somatostatin analogue of claim 1 or a chelate thereof, or a pharmaceutically acceptable salt or a complex with a detectable element.

* * * * *

UNITED STATES PATENT AND TRADEMARK OFFICE
CERTIFICATE OF CORRECTION

PATENT NO. : 6,225,284 B1 Page 1 of 1
DATED : May 1, 2001
INVENTOR(S) : Albert et al.

It is certified that error appears in the above-identified patent and that said Letters Patent is hereby corrected as shown below:

Title page,
Item [57], ABSTRACT,
Line 1, change "Somatostain" with -- Somatostatin --; and
Line 6, insert -- , -- after "His" and before "(Bzl)HyPro,"

Column 19,
Last line, the last hyphen in the formula should be deleted

Column 21,
Lines 9 and 10, correct "guanidino-$C_{2-6}$alkylene" with -- guanidino-$C_{2-6}$alkylene --

Signed and Sealed this

Sixth Day of May, 2003

JAMES E. ROGAN
*Director of the United States Patent and Trademark Office*